United States Patent [19]

Mitra et al.

[11] 4,364,861

[45] Dec. 21, 1982

[54] BLOOD-COAGULATION-PROMOTING PRODUCTS AND METHODS OF PREPARING THEM

[75] Inventors: Gautam Mitra, Kensington; Michael H. Coan, El Cerrito; Shohachi Wada, Oakland, all of Calif.

[73] Assignee: Cutter Laboratories, Inc., Berkeley, Calif.

[21] Appl. No.: 153,341

[22] Filed: May 27, 1980

[51] Int. Cl.$^3$ .................... A61K 35/14; C07G 7/00; A61K 35/16; A61K 37/02

[52] U.S. Cl. .................... 260/112 B; 424/101

[58] Field of Search .................... 260/112 B; 424/101

[56] References Cited

U.S. PATENT DOCUMENTS

| | | | |
|---|---|---|---|
| 3,560,475 | 2/1971 | Fekete et al. | 260/112 B |
| 3,682,881 | 8/1972 | Fekete et al. | 260/112 B |
| 3,717,708 | 2/1973 | Wada et al. | 260/112 B X |
| 4,081,431 | 3/1978 | Stephan et al. | 260/112 B |
| 4,160,025 | 7/1979 | Eibl et al. | 424/101 |
| 4,170,590 | 10/1979 | Stephan et al. | 260/112 B |
| 4,272,523 | 6/1981 | Kotitschke et al. | 260/112 B X |

OTHER PUBLICATIONS

Thrombosis Research, vol. 4, pp. 809–817, 1974 Fenton et al.
Am. J. Clin. Pathol. 19, pp. 471–482, 1949, Ware et al.
New England J. of Med. vol. 273, No. 13, 1965, Tullis et al., pp. 667–674.
British J. of Haematology, vol. 22, 1972, pp. 469–490, Dike et al.
Vox Sang. 24, pp. 441–456 (1973), Middleton et al.
Vox Sang. 33, pp. 37–50, (1977), Suomela et al.

*Primary Examiner*—Howard E. Schain
*Attorney, Agent, or Firm*—Theodore J. Leitereg

[57] ABSTRACT

Blood-coagulation-promoting products substantially free of thrombin are prepared from human blood plasma by contacting a human blood plasma fraction containing coagulation Factors II, VII, IX and X with an anion exchanger to adsorb the coagulation Factors, which are subsequently eluted from the anion exchanger. The eluate is treated to generate a substance having Factor VIII Inhibitor Bypassing Activity and being substantially free of thrombin, and activated Factor X.

6 Claims, No Drawings

BLOOD-COAGULATION-PROMOTING PRODUCTS AND METHODS OF PREPARING THEM

BACKGROUND OF THE INVENTION

1. Field of the Invention:

This invention relates to and has among its objects novel blood-coagulation promoting products and methods of preparing them. It is a particular object of the invention to provide blood-coagulation-promoting products that contain substantial amounts of Factor VIII Inhibitor Bypassing Activity substance but are substantially free of thrombin. Further objects of the invention will be evident from the following description.

2. Description of the Prior Art:

There are estimated to be 100,000 cases of congenital hemophilia in the United States. The two predominant types of hemophilia are Hemophilia A and Hemophilia B. A cure for this congenital disease is not available; however, treatment of the disease has been possible by supplying hemophiliacs with active blood coagulation factors by intravenous administration. An early approach was to administer fresh blood or fresh plasma to temporarily correct the defect of the deficient subject. More recently, concentrates containing particular coagulation factors lacking in different hemophiliacs have been isolated from blood plasma. Since these preparations contain the blood coagulation factors in concentrated form, much lower amounts may be used to achieve rapid stoppage of bleeding, and therapy is more specific than with plasma.

One such preparation is called antihemophilic factor (AHF) or Factor VIII for treatment of Hemophilia A. Factor IX (Antihemophilic Factor B) preparations, such as those described in U.S. Pat. No. 3,717,708, are used for treatment of Hemophilia B patients.

Approximately 15 to 25% of Hemophilia A patients have an inhibitor to Factor VIII. Consequently, when Factor VIII preparations are given to these patients, the effect of Factor VIII is negated because of inhibition of its activity. This inhibitor may be removed by plasma exchange of the patient's plasma for that of a healthy donor or for plasma substitutes. However, the complexity of the exchange procedure makes this approach very undesirable. Animal source Factor VIII can be used, but it shortly elicits a foreign protein response which negates its usefulness.

Recently, in U.S. Pat. No. 4,160,025, (hereinafter '025) there was described a new blood-coagulation-promoting preparation from human blood plasma, which contains a blood coagulation effective substance causing a bypassing of the Factor VIII inhibitor. This new substance was termed FEIBA for "Factor VIII Inhibitor Bypassing Activity" substance. It was noted in '025 that certain "activated" prothrombin complex concentrates, containing Factor IX among others, had been used successfully in controlling bleeding of Factor VIII inhibitor patients. The activation of these prothrombin concentrates was probably due to unknown impurities. The FEIBA of '025 was a preparation which safeguarded in a repeatable and deliberate manner a generation of Factor VIII inhibitor bypassing activity. FEIBA was clinically effective and compatible without undesired side effects.

To prepare FEIBA by the method of '025 human plasma containing citrate ions is treated in the absence of free calcium ions with water-insoluble inorganic coagulation-physiologically-surface-active substances, such as silica gel or kaolin, to generate a FEIBA substance. Water insoluble substances are separated from the FEIBA-containing material, which is then treated with a basic ion exchanger, such as a diethylaminoethyl-group-containing high molecular weight substance, to adsorb the FEIBA substance thereon together with coagulation Factors II, VII, IX, and X. The adsorbed material is eluted and concentrated. The new substance with FEIB-activity is a protein with a higher molecular weight (100,000) than that of unactivated Factors II, VII, IX, and X (70,000) and contains some thrombin.

It is known that calcium ions in conjunction with other materials such as phospholipids and activated Factor X assist in the activation of Bovine Factor VII (Radcliffe et al., *The Journal of Biological Chemistry*, 1975, Vol. 250, No. 2, pp. 388–395, and Radcliffe et al., ibid., 1976, Vol. 251, No. 16, pp. 4797–4802). Further, it is well-known that the action of calcium ions on a mixture of the above coagulation Factors produces substantial amounts of thrombin, which is an undesirable substance when present in materials to be infused into humans. Thus, those skilled in the art have not considered and would not consider the possibility of generating a FEIBA substance by using calcium ions either alone or in conjunction with other agents (e.g. '025).

Currently, there is a Factor VII Inhibitor Bypassing Activity substance of anti-inhibitor coagulant complex marketed by Hyland Laboratories (Costa Mesa, Calif.) under the name AUTOPLEX ®. The FEIBA:thrombin ratio of this material is about 10:1, FEIBA:Factor II is about 10:1, FEIBA:Factor VII is about 2:9, FEIBA:Factor IX is about 1:2, and FEIBA:Factor X is about 5:1. (The above sample was analyzed according to the assays outlined hereinbelow in the Examples section).

SUMMARY OF THE INVENTION

We have discovered methods for preparing novel Factor VIII Inhibitor Bypassing Activity (hereinafter referred to as FEIBA) substances with Factor VIII Inhibitor Bypassing Activity (hereinafter referred to as FEIB-activity). The substances of the invention also may be termed Antihemophilic Factor Inhibitor Bypassing Complexes having Antihemophilic Factor Inhibitor Bypassing Activity or anti-inhibitor coagulant complex.

The novel FEIBA substances include coagulation Factors II, VII, IX, and X and are substantially free of thrombin and activated Factor X. Generally, in preparing the FEIBA substances of the invention a human blood plasma fraction containing coagulation Factors II, VII, IX, and X is contacted with an anion (basic ion) exchanger on which the coagulation Factors are adsorbed. The specific substance or substances adsorbed and subsequently activated to FEIBA are not known. It may be that the mixture of coagulation Factors II, VII, IX, and X contains a specific FEIBA substance precursor which is adsorbed on the ion exchanger together with the coagulation Factors and then activated to a FEIBA substance. Or, the coagulation Factors themselves may constitute such a FEIBA precursor. In any event, applicants have demonstrated that FEIBA substances can be prepared as long as one begins with a mixture of the aforenamed coagulation Factors.

The ion exchanger is selectively washed to remove inhibitors to the generation of FEIBA substance without removing the coagulation Factors which are subsequently eluted from the basic ion exchanger. The eluate is treated in a number of alternative ways to generate a FEIBA substance. In accordance with one aspect of the invention the adsorbed coagulation Factors are eluted from the basic ion exchanger using an aqueous solution with a certain ionic strength. Surprisingly, we have discovered that calcium ions can be employed to generate substantial amounts of FEIBA without generation of substantial amounts of thrombin. The eluate is mixed with a source of calcium ions in an amount sufficient to generate substantial amounts of a FEIBA substance but insufficient to generate substantial amounts of thrombin and held at a temperature and pH and for a time sufficient to generate a FEIBA substance.

Alternatively, in one embodiment of the invention the eluate unexpectedly can be held for a period of time and at a temperature and pH sufficient to generate substantial amounts of a FEIBA substance in the absence of calcium ions or other activating material. The FEIBA substance produced in this manner is characterized particularly as being free of thrombin.

In accordance with another aspect of the present invention the adsorbed coagulation Factors are eluted from the basic ion exchanger using aqueous ammonium bicarbonate. The eluate, after treatment to remove ammonium bicarbonate, is mixed with a source of calcium ions in an amount sufficient to generate FEIBA and held at a temperature and pH and for a time sufficient to generate a FEIBA substance.

A primary advantage of the invention is that FEIBA substances can be produced in substantial amounts and they are substantially free of thrombin. The injection of thrombin into a human is considered highly dangerous. Although it is possible to neutralize thrombin activity with heparin in the presence of antithrombin III, heparin is potentially hazardous to the patient and interferes with the assay of the aforementioned coagulation Factors, which in turn complicates monitoring of infusion into a patient.

Another advantage of the invention is that the so-produced FEIBA substance is substantially free of the activated form of Factor X. Thus, the danger of precipitating intravascular coagulation is reduced.

A particular advantage of the invention is that a FEIBA substance is generated in substantial amounts in the last step of the invention. Thus, one has a choice as to which product is to be manufactured, e.g., a Factor IX concentrate or a FEIBA substance, until the end of the process. In the method of '025 a FEIBA substance is generated in the first step of the patented process, which precludes a choice in the preparation of other useful coagulation products.

DESCRIPTION OF THE PREFERRED EMBODIMENTS

The product of the invention is prepared from human blood plasma. The preponderance of blood generally taken and available for transfusion is protected from coagulation by treatment with a citrate anticoagulant which allows the blood to be utilized for only a limited period of time. After this limited time expires, this blood must be discarded or it can be made available for fractionation into certain useful components. As a matter of fact, the major source of blood converted to plasma for fractionation comes from blood collected by plasmapheresis which has been protected by citrate anticoagulation. It is, therefore, important that processes for the fractionation of plasma be directed to citrate preserved blood, to which the instant method is.

As mentioned above, in the first step in the process of the invention a human blood plasma fraction containing coagulation Factors II, VII, IX, and X is contacted with a basic ion exchanger on which the coagulation Factors are adsorbed. A number of fractionation methods have been applied to human blood plasma, and these methods are summarized in "The Plasma Proteins", second edition, Vol. III, pages 548-550, Academic Press, New York, N.Y. (1977). The preferred starting material in the process of the invention is Effluent I from a Cohn fractionation method (U.S. Pat. No. 2,390,074 and *J. Am. Chem. Soc.*, Vol. 68, page 459 (1946). Effluent I is contacted with an anionic or basic ion exchanger, for example, DEAE (diethylaminoethyl) Sephadex ® consisting of cross-linked dextran chains with diethylaminoethyl groups attached by ether linkages to the glucose units of the polysaccharide chains, supplied by Pharmacia Fine Chemicals, Inc., Piscataway, New Market, N.J., to adsorb the aforementioned coagulation Factors. The spent Effluent I is returned to the plasma fractionation process so that none of the other plasma components is wasted.

Generally, contact between Effluent I and DEAE Sephadex is achieved by forming a bed of freshly equilibrated DEAE Sephadex and passing Effluent I therethrough. Approximately 10 g. (wet weight) of DEAE Sephadex per liter of Effluent I is used although the amounts employed may be varied over a wide range.

The ion exchanger is washed next to remove inhibitors to the generation of a FEIBA substance. Thus, the DEAE Sephadex bed can be treated with about 0.1–0.3 M ammonium bicarbonate at pH 7.0–7.8 until the concentration of protein in the eluate is less than about 4 mg/ml. The concentration of the wash solution, in general, should be sufficient to remove inhibitors to the generation of a FEIBA substance but insufficient to remove the adsorbed coagulation Factors. It is within the compass of the invention to wash the DEAE Sephadex more than once.

The above-described steps are similar to those set forth in U.S. Pat. No. 3,717,708, which is incorporated herein by reference.

In accordance with the instant invention the washed DEAE Sephadex with the aforementioned coagulation Factors adsorbed thereon can be treated in one of two ways to elute the adsorbed substances. In one aspect of the invention (Method A) the DEAE Sephadex can be eluted with ammonium bicarbonate having a concentration of about 0.5–2.0 M preferably about 0.75 M. Generally, the eluting solution should have a concentration of readily removable salt, such as ammonium bicarbonate, sufficient to elute the adsorbed coagulation Factors but insufficient to remove other adsorbed proteins. The pH of the eluting solution should be about 7–9.

The eluate is treated next to remove the salt, e.g., ammonium bicarbonate, from the solution. To this end the eluate may be dialyzed or diafiltered. Alternatively, the eluate may be lyophilized during which procedure the ammonium bicarbonate is volatilized and removed from the product.

The eluate, or lyophilized product, can be constituted, or reconstituted, in a solution containing about 0.05–0.20 M sodium chloride and about 0.05–0.15 M sodium citrate, preferably physiological concentrations. The solution may contain a buffering agent such as TRIS-chloride or the like.

To this solution of coagulation Factors is added a source of calcium ions in an amount sufficient to generate a FEIBA substance but insufficient to generate substantial amounts of thrombin. Usually, enough calcium ions are added such that the effective calcium ion concentration, i.e., the level of calcium ions not bound to non-proteinous material, is about 0.0005–0.0008 mole per liter (M) of eluate.

As the source of calcium ions one may use any calcium containing material that will produce free calcium ions in an aqueous medium and be physiologically compatible with the final product. Thus, the calcium source may be, by way of example and not limitation, calcium chloride, calcium acetate, calcium glycinate, and so forth.

The solution of coagulation Factors with added calcium ions is held at a temperature and pH and for a period of time sufficient to generate a FEIBA substance. The pH of the solution should be about 6 to 9, preferably about 7 to 8, and optimally at about 7.6. The pH may be adjusted by means of the aforementioned buffering agent or by adding an appropriate amount of a physiologically compatible acid, such as hydrochloric acid or the like, to achieve the desired pH.

The temperature at which the solution is held is usually within the range of about 0° to 30° C., preferably about 5°–20° C., and more preferably about 8°–14° C. Maximum generation of FEIBA substance occurs at a temperature of about 10° C.; surprisingly, in most cases at least twice as much FEIB-activity is generated at about 10° C. than at about 5° C. or about 20° C.

The solution is held for a period of about 4 to 48 hours, preferably about 12 to 36 hours to allow a sufficient level of FEIBA substance to be generated. In a typical example, eluate of pH 7.5, treated with 0.0007 molar calcium chloride at 10° C. for 24 hours yielded 170 Units per milliliter (U/ml) of FEIB-activity as defined and determined by a modified '025 assay described hereinbelow.

It is generally desirable to treat the eluate after generation of FEIBA substance with an agent which scavenges calcium ions and thereby stops the generation of FEIBA and thrombin. For this purpose one may use a chelating agent that removes positive ions such as Chelex®-100 (BioRad Laboratories, Inc., Richmond, Calif.), Amberlite (Rohm and Haas Co., Philadelphia, Penn.), sodium citrate, sodium phosphate, or the like in an amount sufficient to remove the calcium ion and prevent further generation of a FEIBA substance. The calcium scavenging agent is characterized by its ability to remove calcium ions and its ease of removal from the solution. Thus, the preferred agent is an ion exchanger, such as Chelex®-100 in a concentration of about 3–4 g per 100 ml of a 5% protein solution, or a biologically compatible chelating agent.

Following removal of calcium ions the solution may be treated to remove water therefrom by procedures well known in the art. For instance, the mixture can be freeze-dried or ultrafiltered and then freeze-dried. Furthermore, the mixture can be sterile filtered by conventional methods prior to water removal.

The dried compositions containing FEIBA substance can be formulated into pharmaceutical preparations for therapeutic, diagnostic, or other uses. To prepare them for intravenous administration the compositions are dissolved usually in water containing physiologically compatible substances such as sodium chloride, glycine, and the like and having a buffered pH compatible with physiological conditions. Generally, guidelines for intravenously administered compositions are established by governmental regulations.

The product prepared in accordance with Method A is characterized as substantially free of thrombin, and activated Factor X, comprising coagulation Factors II, VII, IX, and X and having a Factor VIII Inhibitor Bypassing Activity of at least about 60 U/ml.

The term "substantially free of thrombin" means that the Method A product contains less than 1.5 U/ml of thrombin activity and generally has a FEIBA:thrombin ratio of at least about 50:1, e.g., 50:1 to 800:1 or more.

The FEIBA substance of Method A is characterized in that the FEIBA:Factor Xa ratio is at least about 45:1, e.g., about 45:1 to 200:1 or more (Factor Xa=activated Factor X).

The coagulation Factors are present in the product of Method A generally in the following ratio—FEIBA:Coagulation Factors, about 10:1 to 0.1:1, preferably as follows—FEIBA:Factor II, about 1.5:1 to 6:1; FEIBA:Factor VII, about 0.5:1 to 1.5:1; FEIBA:Factor IX, about 1:1 to 2:1; and FEIBA:Factor X, about 1.5:1 to 7:1.

As mentioned above, it is within the purview of the invention to lyophilize the eluate from the DEAE Sephadex® to yield an ammonium bicarbonate-free protein powder as disclosed in U.S. Pat. No. 3,717,708. Thus, another starting material in this method of the invention is the product of U.S. Pat. No. 3,717,708 either in dry form or reconstituted in a buffer solution such as described in U.S. Pat. No. 3,717,708 or hereinabove. If the dry product of U.S. Pat. No. 3,717,708 is employed, it is reconstituted in a buffer solution such as, for example, aqueous sodium citrate-sodium chloride, Tris (hydroxymethyl) aminomethane hydrochloride (TRIS-chloride) and the like. A source of calcium ions is added to achieve the aforementioned critical concentration. It is important to note that some materials, e.g., citrate ions, form complexes with calcium ions thereby reducing the concentration of free calcium ions. Thus, one must add calcium ions until the concentration of free or uncomplexed calcium ions is about 0.0005 to 0.0008 mole per liter. The concentration of free calcium ions can be determined by procedures standard in the art. The temperature, pH, and holding period are those described above.

In another aspect of the invention (Method B) the washed DEAE Sephadex® with coagulation Factors II, VII, IX, and X adsorbed thereon can be washed further with an aqueous solution of an inorganic salt having an ionic strength (I) sufficient to remove inhibitors to the generation of a FEIBA substance but insufficient to elute the adsorbed coagulation Factors. Usually, the I of the aqueous solution should be less than about 0.3, preferably about 0.2. Typical examples of aqueous solutions that may be used are 0.1–0.3 M aqueous sodium chloride (I=0.1–0.3), TRIS-chloride (I=0.1–0.3), and the like.

Following this washing step the basic ion exchanger is treated to elute the adsorbed coagulation Factors. To this end the basic ion exchanger is contacted with an aqueous solution having an ionic strength sufficient to remove the adsorbed coagulation Factors but insufficient to remove other adsorbed proteins. The I of aqueous solutions employed for this purpose should be, generally, greater than about 0.35, preferably 0.55, and within the range of about 0.35–2.0. Aqueous solutions falling within the above description are, by way of example and not limitation, 0.35–2.0 M aqueous sodium chloride (I=0.35–2.0), and so forth. In general, the aforementioned wash and elution solutions should contain a salt that is physiologically compatible with the final product.

The eluate containing the aforesaid coagulation Factors is treated to adjust the concentration of salt therein to 0.2 or less. Furthermore, in a preferred embodiment of the invention the Factors II, VII, IX, X concentration (FC) should be at least about 10 U/ml, preferably, at least about 50 U/ml. The aforementioned objectives for I and FC may be accomplished for example, using a combination of ultrafiltration and diafiltration as is known in the art. Other modes of operation to achieve the above I and FC will be suggested to the skilled artisan. It is important to note that an FC of about 10 is necessary to generate substantial amounts, at least about 60 U/ml, of FEIBA substance, although an FC less than 10 would yield a product comparable to known products.

Next, the eluate is treated to generate a FEIBA substance. A particularly unexpected feature of Method B is that FEIB-activity can be generated in the absence of any added agents. Thus, the eluate simply is held at a pH and temperature and for a period of time sufficient to generate a FEIBA substance. In general, the above parameters of pH, temperature, and time are the same as those recited hereinabove in Method A. Typically, eluate held at a temperature of 10° C. and a pH of 7.5–7.9 for a period of 24 hours contained about 80 U/ml FEIB-activity. The FEIBA product produced in accordance with this procedure is characterized as being essentially free of thrombin, i.e., containing less than 0.5 Units per ml of thrombin. Generally the FEIBA:thrombin ratio in products made in accordance with this aspect of Method B is about 1000:1 or higher. Usually, the presence of thrombin in such samples cannot be detected. The ratios of FEIBA to coagulation Factors II, VII, IX, and X and to Factor Xa are similar to those for the Method A FEIBA substance.

It is important to note that the above-mentioned mode of activation without the use of extraneous agents is peculiar to Method B of the invention. If the procedure of Method A is followed, a FEIBA substance will not be generated in the absence of added calcium ions. It is believed that the Method B activation in the absence of added agents results from the presence of endogenous calcium ions present in the source plasma. However, activation may be stimulated by other agents and it is not meant to limit the invention by any particular explanation. We have demonstrated that a FEIBA substance can be obtained repeatably and reliably in significant, i.e., therapeutically beneficial, amounts in the absence of added activators by Method B of the invention.

The eluate of Method B also can be mixed with an activating agent such as a source of calcium ions to generate a FEIBA substance. However, one surprising feature of this aspect of the invention is that the amount of calcium ions needed to generate FEIB-activity at levels equivalent to that generated in Method A is about ten-fold less in Method B. Indeed, excellent levels, at least 100–200 U/ml or more, of FEIB-activity can be obtained at concentrations of free calcium ions of about 0.000025–0.0005 mole per liter preferably 0.000025–0.00005 mole per liter. The parameters of temperature, pH, and time are the same as those described above. In a typical example, eluate mixed with 0.00005 mole per liter calcium ions at pH 7.5–7.9, 10° C., for 24 hours yielded about 240 U/ml FEIB-activity.

The ratio of FEIBA to thrombin, to Factor Xa, and to the coagulation Factors II, VII, IX, and X are approximately the same for this product as for the FEIBA substance of Method A.

EXAMPLES

The invention is demonstrated further by the following illustrative examples.

ASSAY METHODS

FEIBA Substance: The procedure used was essentially that of '025 and of Pepper et al., *Brit, J. Haem.*, Vol. 36, pages 573–583 (1977) designed to assay in vitro FEIB-activity, which is defined as a shortening of the activated partial thromboplastin time (APTT) of a Factor VIII inhibitor plasma. The assay was carried out by manual tube-tilting technique.

The reagents used were:

(a) Factor VIII inhibitor plasma obtained from George King Bio-Medical, Overland Park, Kans.

(b) The buffer for dilution was a mixture containing 0.06 M TRIS-chloride, 0.09 M sodium chloride, and 0.5% Human Serum Albumin (Cutter Laboratories, Inc., Berkeley, Calif.) at pH 7.40±0.05.

(c) Kaolin suspension (3 mg/ml) was prepared in physiological saline. The suspension must be shaken vigorously prior to pipetting.

(d) Rabbit Brain Cephalin, Sigma Chemical Co., St. Louis, Mo. was reconstituted with physiological saline according to directions and was kept frozen in a small volume in a plastic tube. Before carrying out the assay procedure, frozen cephalin was thawed, diluted 30-fold with saline, maintained at 37° C. for 10 minutes, and then kept at room temperature, whereat it is stable for several hours.

In the assay 0.1 ml Factor VIII inhibitor plasma, 0.1 ml buffer, and 0.1 ml kaolin suspension were added to a 10×75 mm. glass tube in succession. The reagents were mixed and placed in a 37° C. bath with simultaneous starting of a stopwatch. Fifteen seconds prior to the completion of the incubation, cephalin was added, and after 10 minutes 0.1 ml of 0.025 M calcium chloride was added. The contents were mixed thoroughly, and the tube was held undisturbed. After 30 seconds the tube was tilted at 10-second intervals; the content of the tube became more viscous thus requiring more frequent tilting. A sample that reduced blank time to half is defined (in '025) to contain one unit of FEIB-activity.

Factors II and VII: Factor II and Factor VII were assayed by the method of Owren described in the *Scand. J. Clin. and Lab. Investigation*, Vol. 1, page 81 (1949).

Factors X and Xa: Factor X and Factor Xa were assayed by the method of Bachman et al., described in *Thromb. Diath. Haemorrh.*, Vol. 2, page 24 (1958).

Thrombin: The assay procedure employed was described by Fenton II et al., in *Thrombosis Res.*, Vol. 4, pages 809–817 (1974).

Factors IX and VIII: Modification of the procedures described by Langdell et al. (partial thromboplastin time technique), *J. Lab. Clin. Med.*, Vol. 41, pages 637–647 (1953) and by Proctor et al. (kaolin clotting time method) *Amer. J. Clin. Path.*, Vol. 36, page 212 (1961) were employed. Platelet Factor 3 was supplied by a cephalin suspension. Maximum surface contact activation was achieved with Celite® powder. All other clotting factors (except Factor IX or Factor VIII) were supplied by a substrate comprising plasma from a patient severely deficient in Factor IX or Factor VIII mixed with barium sulfate adsorbed beef plasma. Quantitation of an unknown specimen was made by comparing its clotting time in the test with that achieved by dilutions of a normal standard.

The exact assay procedure is the same for both Factor IX and Factor VIII except that the activator in Factor IX assay is Platelin ® Plus Activator instead of Automated APTT reagent (General Diagnostics, Inc., Morris Plains, N.J.).

EXAMPLE 1

The lyophilized product of U.S. Pat. No. 3,717,708 was dissolved in a buffer mixture containing 0.05 M TRIS and 0.10 M sodium chloride (pH 7.6) to a level of 5% (5 g. of protein per 100 ml of solution). The solution was centrifuged at 10,000×g and cooled to 10° C. Calcium chloride was added to the solution to a concentration of 0.0007 M. Aliquots of the solution were assayed by the above method at selected time intervals up to 24 hours.

To the solution (100 ml) was added 4 g. of Chelex ®-100. The solution was stirred for about 20 min. and the Chelex ®-100 was removed by filtration. The solution containing the generated FEIBA substance was assayed according to the above-described procedures. The results are outlined in Table 1A.

After being assayed the solution was sterile-filtered and lyophilized to give a dry product (6 g).

TABLE 1A

| Time (hrs) | FEIBA (U/ml) | Thrombin (U/ml) |
|---|---|---|
| 0 | 6 | 0 |
| 4 | 11 | 0.10 |
| 8 | 16 | 0.16 |
| 12 | 49 | 0.27 |
| 16 | 85 | 0.48 |
| 20 | 120 | 0.73 |
| 24 | 170 | 1.1 |

The above-described procedure was repeated with the exception that the product was assayed only after 24 hours had passed. The results are found in Table 1B.

TABLE 1B

| FEIBA (U/ml) | Factors (U/ml) | | | | | Thrombin (U/ml) |
|---|---|---|---|---|---|---|
| | II | VII | IX | X | Xa | |
| 118 | 33 | 93 | 98 | 46 | 2 | 0.6 |

EXAMPLE 2

The procedure of Example 1 was followed with the following exceptions: (1) the pH of the solutions was varied over the range of 7.1 to 7.7 and (2) each run was made for a period of 24 hours. The results are summarized in Table 2A.

TABLE 2A

| pH | FEIB-Activity (sec.)$^a$ |
|---|---|
| 7.1 | 120 |
| 7.2 | 111 |
| 7.3 | 113 |
| 7.4 | 108 |

TABLE 2A-continued

| pH | FEIB-Activity (sec.)$^a$ |
|---|---|
| 7.5 | 107 |

$^a$Clotting time at dilution 1:10; a smaller value for clotting time indicates greater FEIB-activity.

The above experiment was repeated and the results are summarized in Table 2B.

TABLE 2B

| pH | FEIB-Activity (sec.) |
|---|---|
| 7.5 | 111 |
| 7.6 | 108 |
| 7.7 | 110 |

EXAMPLE 3

The procedure of Example 1 was followed with the exceptions noted below: (1) the temperature at which the material was held was varied (5° C., 10° C., and 22° C., respectively) and (2) the holding time at each temperature was 24 hours. The results are outlined in Table 3.

TABLE 3

| Temperature (°C.) | FEIB-Activity (sec.)$^a$ | |
|---|---|---|
| | 1:10 | 1:20 |
| 5 | 110 | — |
| 10 | 101 | 110$^b$ |
| 22 | 110 | — |

$^a$Clotting time at dilution 1:10 and 1:20
$^b$Clotting time of 110 sec. at dilution 1:20 for sample run at 10° C. is same as clotting time at dilution 1:10 for sample run at 5 and 22° C.; this indicates that the sample run at 10° C. was twice as active as those run at 5 and 22° C.

EXAMPLE 4

Konyne ® Factor IX Complex (Human) (Cutter Laboratories, Inc., Berkeley, Calif.) was reconstituted according to directions. The sample was buffered with 0.05 M sodium citrate and 0.088 M sodium chloride; protein content was 2.5%. The solution was brought to 10° C. and calcium chloride was added to a concentration of 0.012 M (free calcium ion concentration 0.0007 M). Aliquots of the solution were assayed as described above at time intervals of 0, 4, 8, 12, 16, 20, and 24 hours; the results are found in Table 4.

Chelex ®-100 (1 g) was added to the solution, which was stirred for 20 minutes and then was filtered. Following removal of the Chelex ®-100 the solution was sterile-filtered and lyophilized to give a dry product.

TABLE 4

| Time (hrs) | FEIBA (U/ml) | Thrombin (U/ml) |
|---|---|---|
| 0 | 0$^a$ | 0 |
| 4 | 10$^a$ | 0.11 |
| 8 | 11$^a$ | 0.11 |
| 12 | 17$^a$ | 0.15 |
| 16 | 40 | 0.19 |
| 20 | 56 | 0.25 |
| 24 | 66 | 0.31 |

$^a$See Table 11, footnote 6.

EXAMPLE 5

The procedure of Example 1 was used with the exception that: (1) the calcium ion concentration was varied and (2) the solution was held for 24 hours after addition of calcium before the foregoing assays were performed. Table 5 contains the results in outline form.

TABLE 5

| Calcium ion Concentration (mole/liter) | FEIBA (U/ml) |
|---|---|
| 0 | 44 |
| 0.00052 | 50 |
| 0.00068 | 100 |
| 0.00075 | 221 |
| 0.00083[a] | Clot |

[a]Not in accordance with the invention but provided for purposes of comparison.

EXAMPLE 6

A. The lyophilized U.S. Pat. No. 3,717,708 product was dissolved in a buffer mixture containing 0.05 M TRIS and 0.10 M sodium chloride (pH 7.6) to a level of 5% on a weight to volume basis. After the solution was centrifuged at 10,000×g and cooled to 10° C., kaolin was added to give a 1% kaolin suspension. The mixture was held at 10° C. for 24 hours and assayed according to the aforementioned procedures.

B. The procedure in A above was repeated with the exception that Celite® (Johns-Manville Co., New York, N.Y.) was added to a 1% level in place of kaolin.

C. The procedure in A above was repeated with the exception that the solution was made 0.0007 M in calcium ions by addition of calcium chloride in place of kaolin.

TABLE 6

| Run | Generating Material | FEIBA (U/ml) |
|---|---|---|
| C | 0.0007 M Ca Cl$_2$ | 200 |
| B[a] | 1% koalin | 50 |
| A[a] | 1% Celite® | 76 |
| Control[a] | None | 35 |

[a]Not in accordance with the invention but provided for purposes of comparison. Runs B and A are in accordance with the method of '025.

EXAMPLE 7

Effluent I (30 l.) was contacted with 300 g. of DEAE Sephadex® gel and mixed together. After 2 hours the mixture was filtered to give 300 g. of gel, which was washed sequentially with 3 l. of 0.2 M ammonium bicarbonate, 2 l. of 0.3 M ammonium bicarbonate, and 3 l. of 0.2 M sodium chloride. (Effluent I=Cohn Supernatant I).

After washing, 2 l. of 0.55 M sodium chloride (I=0.55) was applied to the gel to give an eluate (A$_{280}$=12.80). The eluate was concentrated to A$_{280}$ to about 50 by ultrafiltration and diafiltered against 0.05 M TRIS and 0.1 M sodium chloride (pH 7.6) buffer to a protein concentration of A$_{280}$=69.5.

Calcium chloride was added to the eluate (cooled to 10° C.) to a concentration of 0.0005 M, and the eluate was held at 10° C. for 24 hours. Then, Chelex®-100 resin was mixed with the eluate to a level of 10% on a weight to volume (w/v) basis. The eluate was filtered to remove the resin and sodium citrate was added thereto to a level of 0.01 M.

The eluate was analyzed as described above to give the results outlined in Table 7.

TABLE 7

| | | | Factors | | |
|---|---|---|---|---|---|
| Sample | FEIBA (U/ml) | Thrombin (U/ml) | IX (U/ml) | VII (U/ml) | A$_{280}$ |
| Post-activation | 185 | 2.9[a] | N.A.[b] | N.A.[b] | 69.5 |
| Pre-activation | 17.8 | None detected | 71.5 | 46.5 | 69.5 |

[a]1:100 dilution
[b]N.A. = not assayed

EXAMPLE 8

The procedure employed was the same as that of Example 7 with a different batch of Effluent I. The results are summarized in Table 8.

TABLE 8

| | | | Factors | | |
|---|---|---|---|---|---|
| Sample | FEIBA (U/ml) | Thrombin (U/ml) | IX (U/ml) | VII (U/ml) | A$_{280}$ |
| Post-activation | 120 | 1.5[a] | N.A.[b] | N.A.[b] | 31.3 |
| Pre-activation | 10 | None detected | 37.3 | 19.0 | |

[a]1:50 dilution
[b]N.A. = not assayed

EXAMPLE 9

The procedure of Example 7 was repeated using 1 kg of DEAE Sephadex. The protein concentration (A$_{280}$) during activation was 41.5. Table 9A contains a summary of the results.

TABLE 9A

| | | Factors | | | | | |
|---|---|---|---|---|---|---|---|
| Sample | FEIBA (U/ml) | II (U/ml) | VII (U/ml) | IX (U/ml) | X (U/ml) | Thrombin (U/ml) | A$_{280}$ |
| Post-activation | 152.5 | 24.7 | 79.5 | 83.0 | 32.9 | None detected | 41.5 |
| Pre-activation | 18.1 | 23.6 | 12.5 | 49.6 | 36.5 | " | " |

The above eluate was filtered, sterile-filtered, and lyophilized (10 ml samples). The dry product was reconstituted in water for injection (10 ml for each sample) and analyzed according to the above assay methods. The results are outlined in Table 9B.

TABLE 9B

| Sample | FEIBA (U/ml) | Thrombin (U/ml) | Solubility Time (Sec.) | A$_{280}$ | Clarity[a] (%) | Osmolarity (mOsm/kg) |
|---|---|---|---|---|---|---|
| Reconstituted | 152 | None detected | 90 | 37.6 | 95 | 305 |

[a]Clarity = Transmittance at 580 nanometers

EXAMPLE 10

The procedure of Example 7 was followed using two different calcium ion concentrations, namely, 0.0005 M and 0.00075 M. The eluate was assayed at selected time intervals after addition of calcium ions thereto. The results are summarized in Table 10.

TABLE 10

| | Calcium ion concentration | | | |
|---|---|---|---|---|
| | 0.0005 M | | 0.00075 M | |
| Time (hrs) | FEIBA (U/ml) | Thrombin (U/ml) | FEIBA (U/ml) | Thrombin (U/ml) |
| 0 | 25 | None detected | 25 | None detected |
| 17.5 | 173 | 0.6–1.0 | 174 | 0.7–1.1 |
| 19.5 | 186 | " | 206 | " |
| 22.0 | 243 | 0.8–1.5 | 255 | 1.2–1.8 |
| 24.0 | 270 | " | 298 | " |

EXAMPLE 11

The procedure of Example 7 was followed employing an $A_{280}=43$ prior to addition of calcium chloride. The eluate, after calcium ion addition, was analyzed at selected time intervals. Table 11 contains a summary of the results.

TABLE 11

| Time (hrs) | FEIBA (U/ml) | Thrombin (U/ml) |
|---|---|---|
| 0 | 12 | None detected |
| 2.5 | 20[b] | " |
| 5.0 | 23[b] | " |
| 7.5 | 27[b] | 0.48 |
| 9.5 | 32[b] | 0.56 |
| 11.0 | 35[b] | 0.78 |
| 22 | 210 | 1.5 |
| 24 | 241 | 1.9 |

[a]1:20 dilution
[b]It is to be noted that at least 11 hours are required before there is a substantial increase in the amount of FEIBA substance in the eluate.

EXAMPLE 12

The procedure described in Example 7 was followed generally. Two different calcium levels were employed, namely, 0.00025 M and 0.0005 M. In addition, the eluate was assayed after 19.75 hr., 22.75 hr., and 25.75 hr. The results are outlined in Table 12.

TABLE 12

| | Calcium ion concentration | | | | | |
|---|---|---|---|---|---|---|
| | 0 | | 0.00025 | | 0.0005 | |
| Time (hr.) | FEIBA (U/ml) | Thrombin (U/ml) | FEIBA (U/ml) | Thrombin (U/ml) | FEIBA (U/ml) | Thrombin (U/ml) |
| 19.75 | 29.5 | <0.5 | 152 | 1.1 | 201 | 1.1 |
| 22.75 | 47.5 | <0.5 | 225 | 1.1 | 260 | 4.2 |
| 25.75 | 53.0 | <0.5 | 240 | 0.6 | 279 | 3.8 |

The eluate after 25.75 hr. was filtered, sterile-filtered, and lyophilized. The dry product resolubilized in 40 sec. with a clarity of 94% and $A_{280}=42.0$.

EXAMPLE 13

The procedure of Example 7 was followed using calcium ion concentrations of 0.00005 M, 0.00010 M, 0.00015 M, and no added calcium. The eluate was assayed as described above with a summary of the results in Table 13.

TABLE 13

| Calcium ion Concentration (M) | FEIBA (U/ml) |
|---|---|
| 0 | 80 |
| 0.00005 | 240 |
| 0.00010 | 260 |
| 0.00015 | 280 |

EXAMPLE 14

The procedure of Example 7 was followed with the exceptions that (a) the calcium ion concentration was 0.00025 M and (b) the pH was varied within the range 7.0–8.3. Three separate experiments (I–III) were conducted; the results are in Table 14.

TABLE 14

| Experiment Number | pH | FEIBA (U/ml)[a] |
|---|---|---|
| I | 7.61 | 185 |
| | 7.35 | 112 |
| | 7.10 | 62 |
| II | 7.60 | 233 |
| | 7.70 | 210 |
| | 7.81 | 210 |
| | 7.89 | 242 |
| III | 7.51 | 115 |
| | 7.56 | 178 |
| | 7.63 | 218 |
| | 8.12 | 86 |
| | 8.23 | 78 |

[a]The presence of thrombin could not be detected in any of the samples.

EXAMPLE 15

The method of Example 14 was followed with the exception that the temperature and pH of the activation were varied. The results of two separate experiments are summarized in Table 15.

TABLE 15

| Experiment Number | pH | Temperature (°C.) | FEIBA (U/ml)[a] |
|---|---|---|---|
| II | 7.61 | 10 | 185 |
| | 7.61 | 4.5 | 120 |
| | 7.61 | 23 | 140 |
| II | 7.60 | 10 | 233 |
| | 7.61 | 15.5 | 90 |
| | 7.71 | 15.5 | 90 |

[a]The presence of thrombin could not be detected in any of the samples.

EXAMPLE 16

The procedure of Example 15 was employed with the exception that the eluate was diafiltered against 0.1 M sodium chloride alone. TRIS was not employed during the diafiltration; however, the pH of the aqueous sodium chloride was adjusted to 7.56, by addition of dilute hydrochloric acid.

For comparison, the procedure of Example 15 was followed to yield a FEIBA product.

The results are outlined in Table 16.

TABLE 16

| pH | TRIS (M) | FEIBA (U/ml) |
|---|---|---|
| 7.56 | 0 | 178 |
| 7.63 | 0.05 | 218 |

EXAMPLE 17

Effluent I (30 l.) was contacted with 300 g. of DEAE Sephadex gel and mixed together. After 2 hours the mixture was filtered to give 300 g. of gel, which was washed sequentially with 3 l. of 0.2 M ammonium bicarbonate, 2.1 l. of 0.3 M ammonium bicarbonate, and 3 l. of 0.2 M sodium chloride.

After washing, 2 l. of 0.55 M sodium chloride (I=0.55) was applied to the gel to give an eluate ($A_{280}$=12.80). The eluate was concentrated to $A_{280}$ of about 50 by ultrafiltration and diafiltered against 0.05 M TRIS and 0.1 M sodium chloride (pH 7.6) buffer to a protein concentration of $A_{280}$=69.5.

The eluate was cooled to 10° C. for 24 hours. Then, Chelex ®-100 resin was mixed with the eluate to a level of 3% (w/v). The eluate was filtered to remove the resin, sterile-filtered, and lyophilized (10 ml. samples). The dry product was reconstituted in water for injection (10 ml. for each lyophilized sample) and assayed according to the aforedescribed procedures.

For comparison the procedure of Example 7 was employed to prepare a product, which was filtered, sterile-filtered, lyophilized, reconstituted in water for injection as above, and assayed. The results are found in Table 17.

TABLE 17

| Added Activator | FEIBA (U/ml) | Factors (U/ml) | | | | Thrombin (U/ml) | NAPTT[a] (sec.)[b] |
|---|---|---|---|---|---|---|---|
| | | II | VII | IX | X | Xa | | |
| None | 88 | 47 | 155 | 76 | 50 | 0.55 | None Detected | 50 |
| 0.0005 M calcium ion | 155 | 34 | 178 | 84 | 22 | 0.1 | 0.6 | 38 |

[a]NAPTT = Non-activated Partial Thromboplastin time.
[b]1:100 dilution

EXAMPLE 18

Run A: The procedure of Example 7 was followed to prepare eluate containing FEIBA. The eluate (10 ml.) was lyophilized and the lyophilized material was reconstituted in 10 ml. of water for injection. The in vitro stability of the reconstituted product was observed at 0, 2, and 4 hours.

Run B: The procedure of Example 17 was employed to yield a sample of lyophilized product, which was reconstituted in 10 ml. of water for injection. The in vitro stability of the reconstituted material was observed as in Run A.

The results are summarized in Table 18.

TABLE 18

| | Activity (U/ml) | | | | | |
|---|---|---|---|---|---|---|
| | 0 hr. | | 2 hr. | | 4 hr. | |
| Run | FEIBA | Thrombin | FEIBA | Thrombin | FEIBA | Thrombin |
| A | 290 | 0.7 | 290 | 0.5 | 290 | 0.5 |
| B | 83 | N.D.[a] | 82 | N.D.[a] | 89 | N.D.[a] |

[a]N.D. = None detected

EXAMPLE 19

The procedure of Example 7 was followed except that the 0.2 M sodium chloride wash was not discarded.

0.55 eluate was concentrated and diafiltered as in example 7, and the 0.2 M sodium chloride wash was concentrated to an equal volume and diafiltered against the same buffer as the 0.55 eluate.

Sample A: The 0.55 M eluate was diluted with an equal volume of 0.05 M Tris chloride and 0.1 M NaCl.
Sample B: The 0.2 M wash was diluted similarly.
Sample C: Equal volumes of the 0.55 M eluate and the 0.2 M wash were mixed.

Calcium chloride was added to each sample (cooled to 10° C.) to a concentration of 0.0005 M and each was held at 10° C. for 24 hours. Then, Chelex ®-100 resin was mixed with each to a level of 10% (w/v). The suspensions were filtered to remove the resin.

The solutions were assayed as described above to give the results shown in Table 19.

TABLE 19

| Sample | FEIBA (U/ml) |
|---|---|
| A (0.55 M eluate) | 76 |
| B (0.2 M wash) | <5 |
| C (A + B recombined) | 14 |

Having thus described the invention, we claim:

1. A pharmaceutical preparation free of heparin, comprising coagulation Factors II, VII, IX, and X and having Factor VIII Inhibitor Bypassing Activity (FEIB-activity) wherein the FEIBA:Factor II ratio, the FEIBA:Factor VII ratio, the FEIBA:Factor IX ratio, and the FEIBA:Factor X ratio, are about 10:1 to 0.1:1, respectively, and wherein the FEIBA:activity is at least about 60 Units per milliliter and wherein the FEIBA:thrombin ratio is at least about 50:1.

2. The preparation of claim 1 wherein the FEIBA:Factor Xa ratio is at least about 45:1.

3. The preparation of claim 1 wherein the FEIBA:Factor II ratio is about 1.5:1 to 6:1, the FEIBA:Factor VII ratio is about 0.5:1 to 1.5:1, the FEIBA:Factor IX ratio is about 1:1 to 2:1, and the FEIBA:Factor X ratio is about 1.5:1 to 7:1.

4. The preparation of claim 1 which contains less than 1.5 Units per milliliter of thrombin activity.

5. The preparation of claim 1 which contains less than 0.5 Units per milliliter of thrombin and the FEIBA:thrombin ratio is about 1000:1 or higher.

6. A pharmaceutical preparation free of detectable thrombin and heparin, comprising coagulation Factors II, VII, IX, and X and having Factor VIII Inhibitor Bypassing Activity (FEIB-activity) wherein the FEIBA:Factor II ratio is about 1.5:1 to 6:1, the FEIBA:Factor VII ratio is about 0.5:1 to 1.5:1, the FEIBA:Factor IX ratio is about 1:1 to 2:1, and the FEIBA:Factor X ratio is about 1.5:1 to 7:1.

* * * * *